(12) United States Patent
Hekmatshoartabari et al.

(10) Patent No.: US 10,772,720 B2
(45) Date of Patent: Sep. 15, 2020

(54) METHOD OF ASSEMBLING ARTIFICIAL ELECTRONIC SKIN

(71) Applicant: International Business Machines Corporation, Armonk, NY (US)

(72) Inventors: Bahman Hekmatshoartabari, White Plains, NY (US); Ghavam G. Shahidi, Pound Ridge, NY (US); Davood Shahrjerdi, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 306 days.

(21) Appl. No.: 15/978,129

(22) Filed: May 12, 2018

(65) Prior Publication Data
US 2018/0256314 A1 Sep. 13, 2018

Related U.S. Application Data

(60) Division of application No. 14/935,395, filed on Nov. 7, 2015, now Pat. No. 9,968,438, which is a (Continued)

(51) Int. Cl.
*G01R 31/28* (2006.01)
*A61F 2/10* (2006.01)
(Continued)

(52) U.S. Cl.
CPC .............. *A61F 2/105* (2013.01); *A61F 2/50* (2013.01); *A61F 2/5044* (2013.01); *A61F 2/76* (2013.01);
(Continued)

(58) Field of Classification Search
CPC ............ H01L 29/4908; H01L 51/0508; H01L 27/301; A61F 2/105; Y10T 29/49103;
(Continued)

(56) References Cited

U.S. PATENT DOCUMENTS 7,112,755 B2 9/2006 Kitano
7,260,999 B2 8/2007 Divigalpitiya
(Continued)

OTHER PUBLICATIONS

Kuniharu Takei et al., Nanowire active-matrix circuitry for low-voltage macroscale artificial skin, Nature Materials, Oct. 2010, pp. 821-826 and pp. 1-4 of Supplementary Information.
(Continued)

*Primary Examiner* — Thiem D Phan
(74) *Attorney, Agent, or Firm* — L. Jeffrey Kelly; Otterstedt, Wallace & Kammer, LLP

(57) ABSTRACT

High resolution active matrix nanowire circuits enable a flexible platform for artificial electronic skin having pressure sensing capability. Comb-like interdigitated nanostructures extending vertically from a pair of opposing, flexible assemblies facilitate pressure sensing via changes in resistance caused by varying the extent of contact among the interdigitated nanostructures. Electrically isolated arrays of vertically extending, electrically conductive nanowires or nanofins are formed from a doped, electrically conductive layer, each of the arrays being electrically connected to a transistor in an array of transistors. The nanowires or nanofins are interdigitated with further electrically conductive nanowires or nanofins mounted to a flexible handle.

4 Claims, 6 Drawing Sheets

Related U.S. Application Data continuation of application No. 14/697,608, filed on Apr. 27, 2015, now Pat. No. 9,421,087.

(51) Int. Cl.

| | |
|---|---|
| *H01L 29/06* | (2006.01) |
| *H01L 29/16* | (2006.01) |
| *H01L 27/12* | (2006.01) |
| *A61F 2/50* | (2006.01) |
| *H01L 21/3213* | (2006.01) |
| *A61F 2/76* | (2006.01) |
| *G01L 5/22* | (2006.01) |
| *H01L 23/498* | (2006.01) |
| *A61F 2/70* | (2006.01) |
| *A61F 2/68* | (2006.01) |
| *B82Y 15/00* | (2011.01) |

(52) U.S. Cl.
CPC ........ *G01L 5/228* (2013.01); *H01L 21/32133* (2013.01); *H01L 23/4985* (2013.01); *H01L 27/1203* (2013.01); *H01L 27/124* (2013.01); *H01L 27/1255* (2013.01); *H01L 27/1259* (2013.01); *H01L 29/0676* (2013.01); *H01L 29/16* (2013.01); *A61F 2/70* (2013.01); *A61F 2002/5001* (2013.01); *A61F 2002/5007* (2013.01); *A61F 2002/5061* (2013.01); *A61F 2002/6827* (2013.01); *A61F 2002/7635* (2013.01); *B82Y 15/00* (2013.01); *Y10S 977/762* (2013.01); *Y10S 977/925* (2013.01); *Y10T 29/49004* (2015.01); *Y10T 29/49103* (2015.01)

(58) Field of Classification Search
CPC .. Y10T 29/49004; A61B 5/6885; B82Y 15/00
USPC .............................. 29/593, 621.1, 610.1, 825
See application file for complete search history.

(56) References Cited

U.S. PATENT DOCUMENTS

| | | |
|---|---|---|
| 7,501,069 B2 | 3/2009 | Liu |
| 7,557,367 B2 | 7/2009 | Rogers |
| 7,645,398 B2 | 1/2010 | Kim |
| 8,198,789 B2 | 6/2012 | Choi |
| 8,217,381 B2 | 7/2012 | Rogers |
| 8,258,554 B2 | 9/2012 | Meng |
| 9,125,575 B1 * | 9/2015 | Hekmatshoartabari ..................... A61B 5/04001 |
| 9,281,415 B2 * | 3/2016 | Bao .................. G06F 3/044 |
| 9,314,381 B2 | 4/2016 | Curran et al. |
| 9,421,087 B1 | 8/2016 | Hekmatshoartabari et al. |
| 2008/0054875 A1 | 3/2008 | Saito |
| 2009/0293631 A1 | 12/2009 | Radivojevic |
| 2011/0084314 A1 | 4/2011 | Or-Bach et al. |
| 2011/0233617 A1 | 9/2011 | Or-Bach et al. |
| 2012/0062245 A1 | 3/2012 | Bao |
| 2012/0138940 A1 | 6/2012 | Sato |
| 2015/0230720 A1 | 8/2015 | Hekmatshoartabari et al. |
| 2016/0118912 A1 | 4/2016 | Hayashi |
| 2016/0310261 A1 | 10/2016 | Hekmatshoartabari et al. |

OTHER PUBLICATIONS

Paul J. Otterstedt, List of IBM Patents or Applications Treated as Related, May 12, 2018, pp. 1-2.

* cited by examiner

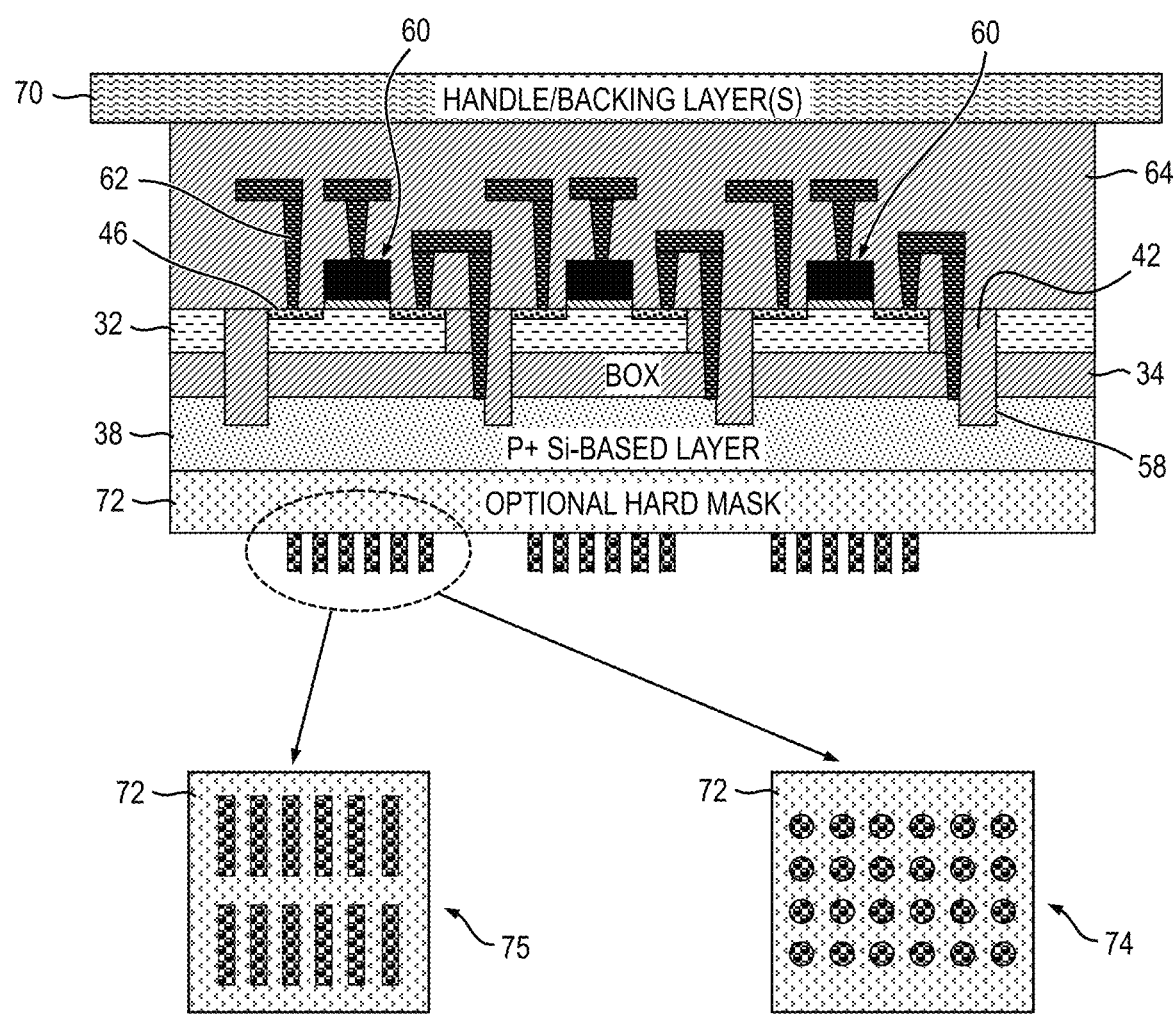

METHOD OF ASSEMBLING ARTIFICIAL ELECTRONIC SKIN

CROSS-REFERENCE TO RELATED APPLICATION

This application is a divisional of U.S. patent application Ser. No. 14/935,395 filed 11 Jul. 2015, which is in turn a continuation of U.S. patent application Ser. No. 14/697,608 filed Apr. 27, 2015. The complete disclosures of U.S. patent application Ser. No. 14/935,395 and U.S. patent application Ser. No. 14/697,608 are expressly incorporated herein by reference in their entireties for all purposes.

FIELD

The present disclosure relates to the physical sciences and, more particularly, to devices including active matrix circuitry and nanostructures for detecting pressure and methods of fabrication of such devices.

BACKGROUND

Artificial electronic skin offers potential advantages in the fields of prosthetic devices and robotics. Attempts to create electronic skin for application in such fields have often included the use of organic semiconductor materials. Organic-based devices have been characterized by relatively high operating voltages because of the defective nature of the organic materials. Advancements in layer transfer technology and printing of inorganic semiconductors has allowed significant decreases in operating voltages associated with electronic skins. Integrated sensor arrays including nanowire-array active components have been proposed for monitoring applied pressure profiles.

Nanowires have been incorporated within microelectrode arrays that include silicon substrates. The nanowires can be grown within open pores by electrochemical deposition or by patterning and etching of silicon substrates. The nanowires in some applications function as electrodes that can be used to apply electrical signals to biological tissue or to receive signals from such tissue.

BRIEF SUMMARY

In accordance with the principles discussed herein, methods are disclosed for fabricating artificial electronic skin assemblies including active matrix structures and using artificial electronic skin assemblies. Artificial electronic skin assemblies including interdigitated nanostructures are further disclosed.

An exemplary fabrication method is provided that includes obtaining a first assembly including a plurality of transistors, a semiconductor layer, a plurality of active regions within the semiconductor layer, the active regions forming parts of the transistors, and a plurality of electrically isolated, first arrays of electrically conductive first nanostructures, each first array being electrically connected to one of the transistors. A second assembly including a flexible handle and a plurality of electrically conductive second nanostructures secured to and extending from the flexible handle is also obtained. One or more spacers are positioned between the first and second assemblies. The first assembly is mounted to the second assembly, causing the first and second nanostructures of the first and second assemblies to be interdigitated.

A further method includes obtaining an artificial electronic skin assembly including a first assembly including a plurality of transistors, a semiconductor layer, a plurality of active regions within the semiconductor layer, the active regions forming parts of the transistors, and a plurality of electrically isolated, first arrays of electrically conductive first nanostructures, each first array being electrically connected to one of the transistors. The artificial electronic skin assembly further includes a second assembly including a flexible handle and a plurality of electrically conductive second nanostructures secured to and extending from the flexible handle, the plurality of the second nanostructures being connected to a common reference potential. The first assembly is mounted to the second assembly such that the first nanostructures of the first arrays and the second nanostructures are interdigitated and form variable resistors. The method further includes exerting pressure on the flexible handle in the direction of the first assembly, thereby causing relative movement of the interdigitated first and second nanostructures and changing the electrical resistance of one or more of the variable resistors, and detecting the pressure exerted on the flexible handle based on the change in electrical resistance.

An artificial electronic skin assembly is disclosed that includes a first assembly including a plurality of transistors, a semiconductor layer, a plurality of active regions within the semiconductor layer, the active regions forming parts of the transistors, and a plurality of electrically isolated, first arrays of electrically conductive first nanostructures extending vertically with respect to the semiconductor layer, each first array being electrically connected to one of the transistors. The artificial electronic skin assembly further includes a second assembly including a flexible handle and a plurality of electrically conductive second nanostructures secured to and extending vertically from the flexible handle, the plurality of the second nanostructures being connected to a common reference potential. The first assembly is mounted to the second assembly such that the first nanostructures of the first arrays and the second nanostructures are interdigitated and form variable resistors.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

Substantial beneficial technical effects are provided by the exemplary structures and methods disclosed herein. For example, one or more embodiments may provide one or more of the following advantages:

Flexible, artificial electronic skin having low operating voltage requirements;
Pressure detection without changing the inherent properties of artificial electronic skin materials;
Change in resistance of nanowire or nanofin arrays allow accurate pressure detection;
Cost-effective and repeatable fabrication.

These and other features and advantages of the disclosed methods and structures will become apparent from the following detailed description of illustrative embodiments thereof, which is to be read in connection with the accompanying drawings.

BRIEF DESCRIPTION OF THE DRAWINGS

FIG. 6 schematically illustrates the formation of an optional hard mask and a template for patterning;

FIG. 6A schematically illustrates an array of fins printed on a hard mask;

FIG. 6B schematically illustrates an array of dots printed on a hard mask

DETAILED DESCRIPTION

A method is disclosed for forming an integrated CMOS pressure sensor having opposing interdigitated arrays of nanostructures such as nanowires or nanofins. A backplane refers to an array of transistors (active devices). The array of transistors is electrically connected to arrays of the nanowires or nanofins. The backplane may also contain address lines, program lines, power supply lines, and storage capacitors which are fabricated using the same process technology as that of the transistors. Passive devices addressed/programmed by the backplane are typically referred to as the frontplane. An active matrix refers to the combination of a backplane and a frontplane.

Active matrix structures such as backplanes are fabricated using techniques described in detail below. Active semiconductor devices are formed using a semiconductor-on-insulator (SOI) substrate. The substrate is thinned using a layer transfer technique or chemical/mechanical processing. Transistors are formed using the semiconductor layer of the substrate, possibly along with additional circuits that provide other functions such as logic, transceiving and/or energy harvesting.

Figure 1:
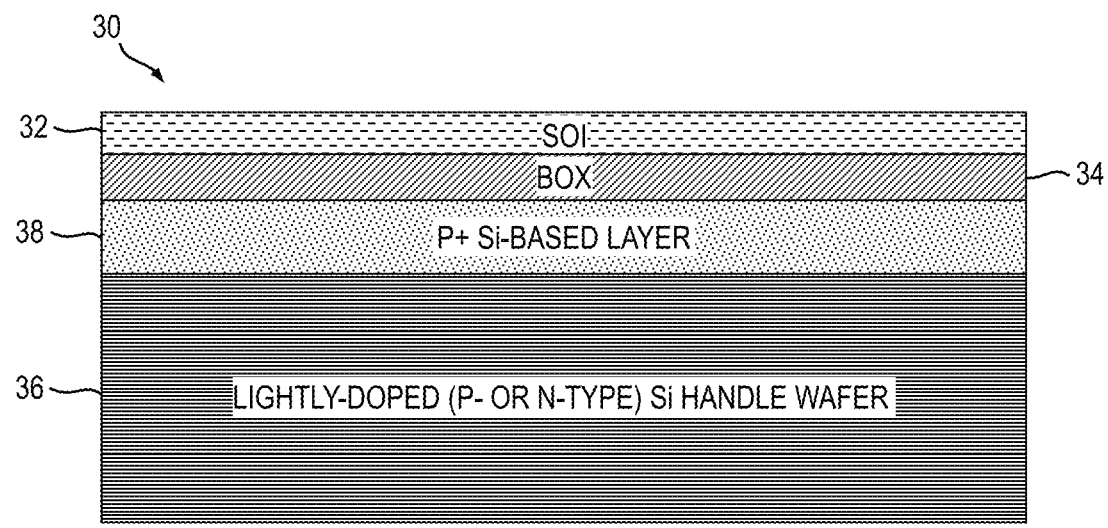
FIG. 1 shows a schematic illustration of a semiconductor on insulator (SOI) substrate including a doped layer.
Figure 2:
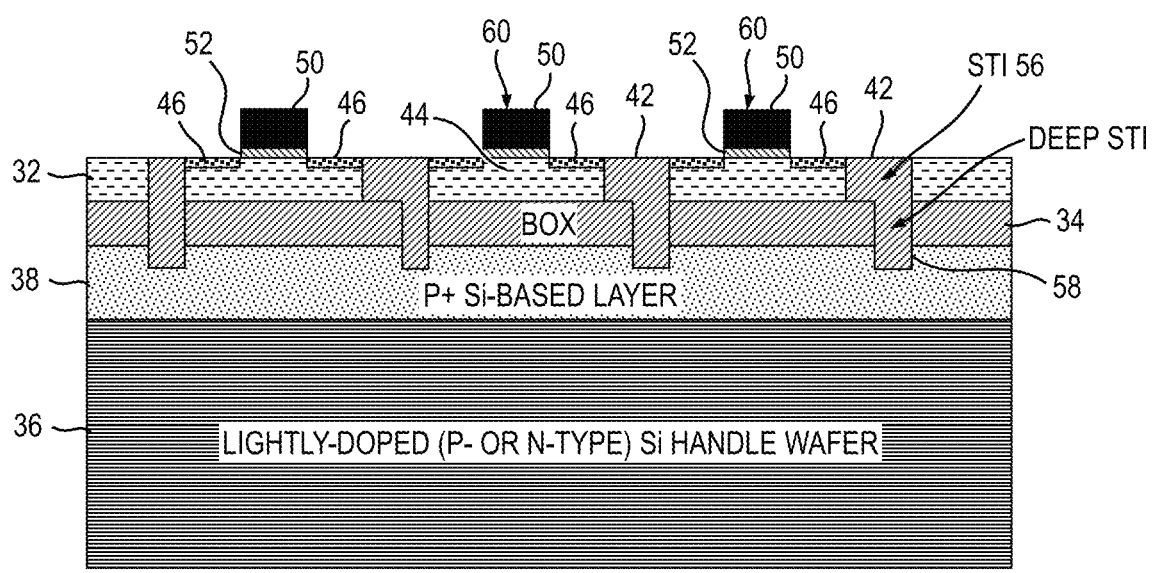
FIG. 2 shows the semiconductor on insulator substrate including deep trenches filled with electrically insulating material and transistors fabricated using the semiconductor on insulator substrate.

An exemplary method for fabricating a backplane structure is schematically illustrated in FIGS. 1-4. The starting substrate in this example is a silicon-on-insulator (SOI) wafer 30 comprised of a thin crystalline semiconductor layer (SOI layer) 32 on a buried oxide (BOX) insulator 34, which is in turn on a bulk silicon (handle) substrate 36 (FIG. 2). The thickness of the semiconductor layer 32 is between 2 nm-1 μm in exemplary embodiments, but thicker or thinner layers may be usable in some applications. Relatively thin semiconductor layers facilitate the production of mechanically flexible active matrix structures suitable for artificial electronic skin as discussed further below. Exemplary single crystal materials for the crystalline semiconductor layer 32 include silicon and silicon-containing films such as silicon germanium. The insulator layer 34 in an exemplary embodiment is between 5-200 nm, but may also be thicker or thinner for some applications. Other semiconductor-on-insulator substrates may alternatively be employed, such as silicon-germanium-on-insulator (SGOI), germanium-on-insulator (GOI) and various III-V materials on insulating substrates. The semiconductor-on-insulator substrates may be produced using techniques known in the art. The buried insulator layer 34 in one exemplary embodiment is a high quality silicon dioxide layer that is thermally grown, though other buried insulators such as boron nitride (BN) and aluminum oxide ($Al_2O_3$) may alternatively be employed in some embodiments. High quality buried oxides (BOX) are generally characterized by relatively low interface trap densities ($D_{it}$). The size and shape of the wafer can be chosen by the manufacturer.

The SOI substrate 30 is processed using known device fabrication processes to form a heavily doped layer 38 in the handle substrate 36 that adjoins the electrically insulating layer 34. (See FIG. 1.) Ion implantation following manufacture of the SOI substrate is one exemplary technique for forming the doped layer 38. Alternatively, the heavily doped layer 38 can be grown epitaxially during manufacture of an SOI wafer. In one or more exemplary embodiments, boron doping (for example, greater than $1\times10^{18}$ $cm^{-3}$) may be provided to form a p+ layer 38. In alternative embodiments, phosphorus doping could be employed form an n+ layer. The heavily doped layer can be formed as a continuous layer as shown, or alternatively in selected areas of the handle substrate beneath the electrically insulating layer, during fabrication of the SOI wafer 30. Ion implantation, possibly conducted through a mask if the layer is formed only in selected areas, can be employed following SOI substrate wafer fabrication to form the doped layer. The layer 38 is between 500 nm-5 μm in depth in a crystalline silicon handle substrate 36 in one or more embodiments.

Referring to FIG. 2, the semiconductor layer 32 is etched to form isolated portions ("islands") that define the active regions of the backplane. Device isolation is typically (though not necessarily) among the first steps performed using conventional processing, prior to transistor fabrication. Conventional techniques for effecting shallow trench isolation (STI) may be employed for providing two adjoining trenches 56, 58. One trench 56 extends through the semiconductor layer 32 to the electrically insulating layer 34. The second trench 58 extends through both the semiconductor layer and electrically insulating layer and into the heavily doped layer 38. Lithography followed by dry etch may be employed to form the trenches. Deposition of electrically insulating materials 42 follows trench formation. Exemplary electrically insulating materials 42 include silicon dioxide, silicon nitride, or a high-k dielectric material. High-k materials, such as hafnium oxide, are understood as having dielectric constants exceeding that of silicon dioxide. CMP may be employed to planarize the top surface of the wafer.

The backplane elements can be formed using conventional CMOS technology using the SOI wafer 30 to make thin film transistors (TFTs) and other associated elements. The circuit elements can include field-effect or bipolar junction transistors fabricated using standard CMOS processing (implanted or raised source/drain regions, thermal oxide or high-k dielectric, implanted, epitaxial or poly emitters and collectors). ETSOI (extremely thin SOI), PDSOI (partially depleted SOI) and Finfet are among the technologies that can alternatively be employed to form the transistors. ETSOI devices may include raised source/drain regions formed on a crystalline silicon layer having a thickness of less than ten nanometers. The crystalline silicon layer used to form PDSOI devices can be greater than fifty nanometers. In an exemplary structure including n-type transistors, implanted n+ source/drain regions 46 and associated channel regions 44 are formed using the semiconductor layer 32. Ion implantation of the semiconductor layer 32 may be employed for forming source/drain regions while the regions of the semiconductor layer to be used as the channel regions are protected by a mask. A high-k gate dielectric material is deposited and electrically conductive (e.g. metal) gate layers are formed on the layer of gate dielectric material. Schematic illustrations of gate stacks 50 and gate dielectric layers 52 of the depicted FETs 60 are provided. In some embodiments, the gate structures are formed prior to the formation of the source/drain regions. While the transistors are formed in the active regions of the semiconductor layer 32 following shallow trench isolation in the illustrated embodiments, they may alternatively be formed in the active regions prior to isolation.

The source and drain regions in some embodiments can be formed using the semiconductor layer 32 employing conventional, low temperature CMOS technology. For example, highly doped raised source and drain regions (not shown) can be selectively grown epitaxially on the exposed surface of the semiconductor layer 32. Boron doped silicon germanium may be employed to form pFET structures while nFET structures can be formed using phosphorus or arsenic doped silicon germanium. The dopants that provide the conductivity of the source and drain regions can be introduced during the epitaxial growth process. Ion implantation can be employed in place of such in situ doping. Gate electrodes can be deposited by PVD, ALD, CVD or other processes known to those of skill in the art on the gate dielectric layers. The gate electrodes may be comprised of metals such as TiN, TaN, Al, or a combination of such metals. Gate electrode layers may also include a polysilicon layer located on top of a metal material, whereby the top of the polysilicon layer may be silicided.

Figure 3:
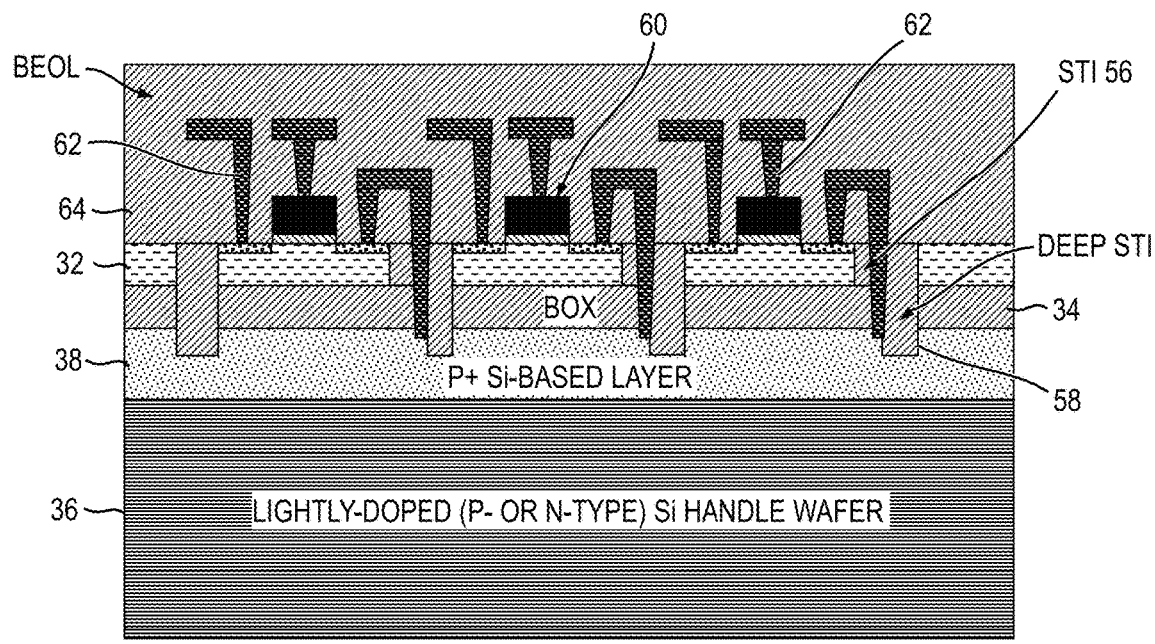
FIG. 3 schematically illustrates back-end-of-line metallization on the semiconductor on insulator substrate shown in FIG. 2.

Electrical communication between the transistors 60 and the heavily doped layer 38 of the handle substrate is provided by deep vias through the electrically insulating layer 34 as shown in FIG. 3. Back end of line (BEOL) metallization processing is conducted to form via conductors 62 and other metal layers within a dielectric layer 64 serving as a passivation and/or planarization layer to form a backplane structure. The dielectric layer 64 chosen should have good adhesion with silicon in embodiments where silicon is employed. It should additionally have a fracture toughness value ($K_{Ic}$) at least comparable to that of silicon in embodiments where silicon is employed to facilitate controlled spalling (if used), as discussed further below. Silicon dioxide, silicon nitride and silicon oxy-nitride have fracture toughness values comparable to that of silicon and are accordingly among the materials that may be chosen for the dielectric layer 64. Using typical insulator growth methods, such as chemical vapor deposition, adhesion between silicon and insulator materials such as silicon dioxide, silicon nitride and silicon oxy-nitride is satisfactory. The via conductors 62 electrically connecting the transistors 60 with highly doped layer 38 are formed in the electrically insulating materials within the trenches 56, 58, the dielectric layer 64, and the electrically insulating layer 34.

Figure 4:
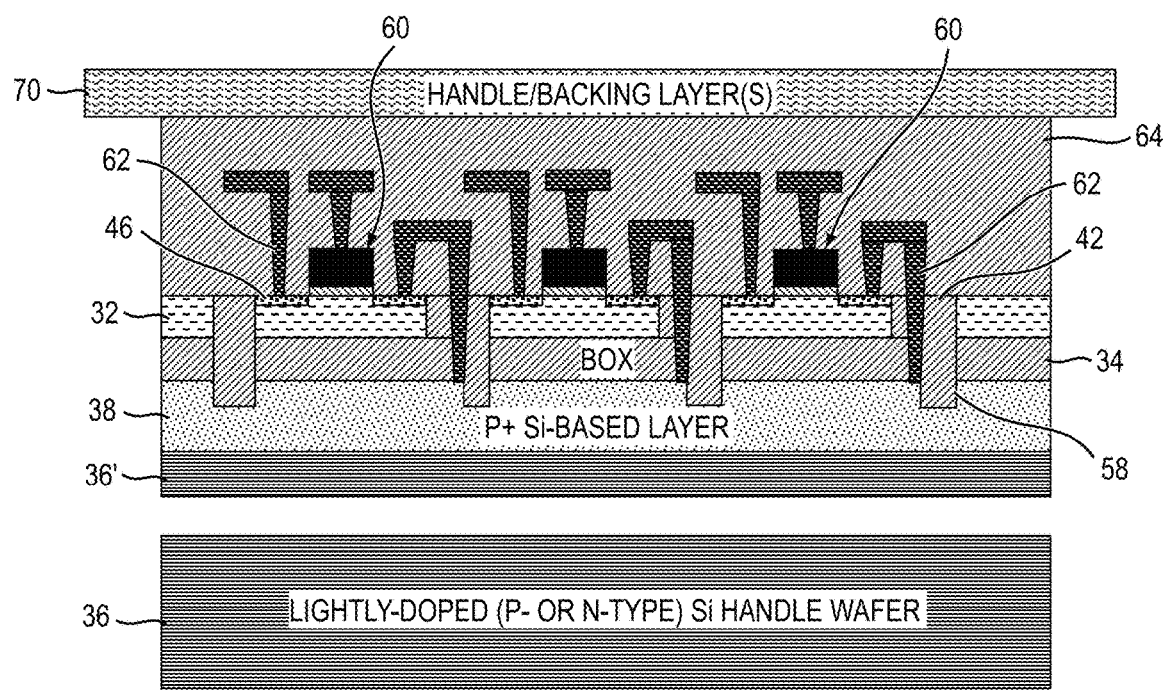
FIG. 4 schematically illustrates thinning the handle portion of the semiconductor on insulator substrate following metallization.

Fabrication of the structure shown in FIG. 3 is followed, in some embodiments, by the formation of a handle/backing layer(s) 70 as shown in FIG. 4. The handle/backing layer(s) in some embodiments includes a stressor metal layer(s) (e.g. nickel) and a flexible handle substrate such as a polyimide layer. An optional insulator layer may be provided to prevent contact of the stressor layer with the electrically conductive elements of the backplane formed during BEOL processing. The flexible handle substrate (e.g. polyimide) is then used for detaching a thin layer of Si by spalling through the handle wafer as shown in FIG. 4. The proper amount of stress to be applied to effect spalling at a desired location in the handle wafer 36 may vary depending on the construction of the backplane structure.

As discussed above, controlled spalling is facilitated by selecting an appropriate dielectric layer 64 above the backplane layer. If the electrically insulating layer 64 has a fracture toughness value comparable to silicon, to the first order, the silicon/insulator stack of the exemplary structure can be treated as a single layer in calculating the depth of fracture as a function of stress applied by the stressor layer(s). Therefore, a proper amount of stress can be considered for a desired fracture depth. If the dielectric layer 64 has a toughness value larger than that of silicon, the fracture will occur inside the silicon. However, the insulating layer should not have a toughness value materially smaller than that of silicon (or other substrate material, if employed) because the fracture will occur within the dielectric layer 64 instead of in the silicon handle wafer 36. The thickness of the metal stressor layer is an additional factor in determining where the fracture will occur in the substrate. Following spalling from the handle wafer 36, a thin residual silicon layer 36' from the substrate 36 remains beneath the electrically insulating (BOX) layer 34 and the heavily doped layer 38. Stress-induced substrate spalling is disclosed in U.S. Pat. No. 8,247,261, which is incorporated by reference herein.

Figure 5:
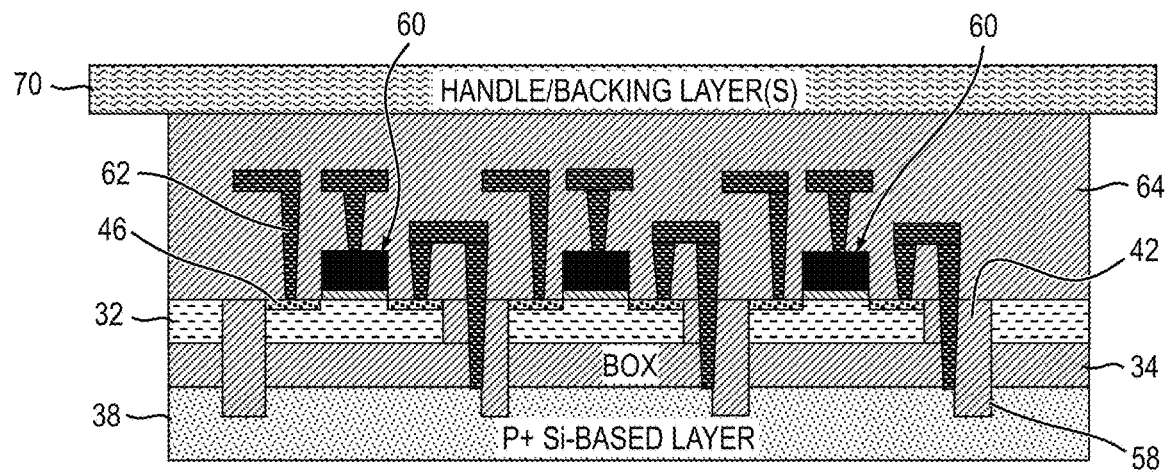
FIG. 5 schematically illustrates selective removal of residual handle portion material.

The thin Si residual layer 36' spalled from the handle wafer 36 is then removed using known techniques, e.g. by selective wet or dry etching to form the structure shown in FIG. 5. The highly doped layer 38 remains following such selective etching. The use of a p-type layer 38 facilitates the etching process in some embodiments as it functions as an etch stop layer. Exemplary techniques for removing the residual layer 36' include reactive ion etch and wet etch in TMAH or KOH (tetramethylammonium hydroxide or potassium hydroxide).

It will be appreciated that the handle substrate 36 can be thinned using alternative methods, including chemical/mechanical means such as chemical mechanical planarization (CMP), followed by selective etching to remove any residual silicon layer 36'. The handle/backing layer(s) 70 used in such embodiments would not require the same elements required for controlled spalling. A flexible layer of polymeric material could be employed to form the layer 70 in some embodiments. Potassium hydroxide (KOH) and tetramethylammonium hydroxide (TMAH), as discussed above, are among the materials that may be employed for the selective etching of the residual silicon layer to form the exemplary structure of FIG. 5. In embodiments including an n-type, silicon-based layer 38 that does not function as an etch stop, the etching of the residual layer 36' could be discontinued upon the detection of a dopant found in the highly doped layer 38 that is not present in the handle portion of the wafer. Alternatively, a highly doped, n-type silicon based layer could be biased to impede the etching process once the residual silicon layer 36' has been removed.

Referring to FIG. 6, a nitride (e.g. silicon nitride) or oxide (e.g. aluminum oxide) hard mask 72 is optionally formed on the highly doped layer 38. In embodiments wherein the highly doped layer is a p+ silicon-based layer, etch selectivity of the hard mask with respect to p-type silicon is provided. Arrays 74 of dots, such as shown in FIG. 6B, are formed on the hard mask in some embodiments where the hard mask is employed, the dots corresponding in diameter and location to the nanowires to later be formed from the highly doped layer 38. In some embodiments, the arrays 74 are formed using a lithography technique such as e-beam, photolithography, and nano-imprint. In other embodiments, self-assembled arrays of particles are formed. The hard mask and arrays 74 of dots formed thereon are employed as a template for subsequent patterning as described below. Gold and silicon dioxide are two exemplary materials from which the dots can be formed. Resist materials that facilitate selective etching are further exemplary materials for forming arrays of dots.

Self-assembly of gold nanoparticles on a metal oxide hard mask (e.g. aluminum oxide, hafnium oxide) can be achieved by procedures known to the art. In one exemplary procedure, the oxide surface is coated with a monolayer of a bifunctional compound having a functionality that adheres to the surface of the oxide (e.g. hydroxamic acid, phosphonic acid) and a charge moeity. For example, pyridine hydroxamic acid methiodide has a hydroxamic acid functionality which self assembles on metal oxide surfaces and a charged moeity (pyridinium salt). After self-assembly of this molecule to form a monolayer on the oxide surface, the positive surface charge of the self-assembled monolayer (SAM) attracts negatively charged molecules or particles. Gold nanoparticles are coated with a ligand. In the case of water soluble gold nanoparticles, the ligand is usually is a charged molecule such as citrate salt which carries a negative charge on the surface of gold nanoparticles. Therefore, when a substrate with positively charged SAM is immersed in a solution of negatively charged gold nanoparticles, the gold particles are attracted to positively charged SAM through coulombic attraction, forming electrostatic bonds and adhering to the surface of the oxide substrate. In one exemplary alternative procedure, molecules having hydroxamic functionality that causes adherence to an oxide surface and thiol functionality that can attract gold nanoparticles from solution (water or solvent) are employed.

As discussed above, a hard mask is not necessarily employed prior to nanowire formation. In some embodiments, a photoresist layer (not shown) is deposited directly on the highly doped layer 38 and patterned to form arrays of photoresist dots corresponding to the arrays of nanowires to be formed by subsequent etching. In some embodiments, lithographical techniques are employed to print arrays 75 of fins instead of dots. FIG. 6A schematically illustrates an array of fins formed on the hard mask 72 for subsequent formation of nanofins from the heavily doped semiconductor layer 38.

Once the structure as shown in FIG. 6 is obtained, the hard mask 72 is patterned. The etch rate of the arrays 74 of dots or arrays 75 of fins, being slower than the etch rate of the hard mask 72 on which they are formed, facilitate pattern transfer. The arrays 74,75 of dots or fins, if not removed during pattern transfer, are subsequently removed once the hard mask 72 has been patterned. Further etching of the patterned hard mask 72 causes the pattern to be transferred from the hard mask to the highly doped layer 38 as shown schematically in FIG. 7, forming arrays 76 of nanowires or nanofins corresponding to the arrays 74 of dots or the arrays 75 of fins. The nanowires or nanofins 78 extend in the vertical direction with respect to the semiconductor layer 32 used to form the transistors 60. Being formed from the electrically conductive, highly doped semiconductor layer 38, the nanowires/nanofins are electrically conductive. The nanowires or fins comprising each array are electrically connected to each other by a remaining portion of the highly doped semiconductor layer 38, from which they extend. Each array 76 of nanowires or nanofins 78 is also electrically connected to a transistor 60 by a via conductor 62 formed during earlier processing. The arrays 76 are electrically isolated from each other by the electrically insulating material within the trenches 58. The height of each nanowire or nanofin 78 is between 500 nm-5 μm in one or more embodiments. The nanowires or nanofins in each array 76 are substantially equal in height. The width of each nanowire or fin is in the range of 100 nm-5 μm in one or more embodiments. The width is substantially uniform in some embodiments, though it may vary between base and tip in other embodiments. The spacing between nanowires or fins within arrays ranges from 100 nm-10 μm in exemplary embodiments. The dimensions (length and width) of the nanowire/nanofin arrays is between one micron and fifty microns in some embodiments. The array dimensions are substantially larger than the corresponding dimensions of the transistors 60 in one or more embodiments.

Figure 7:
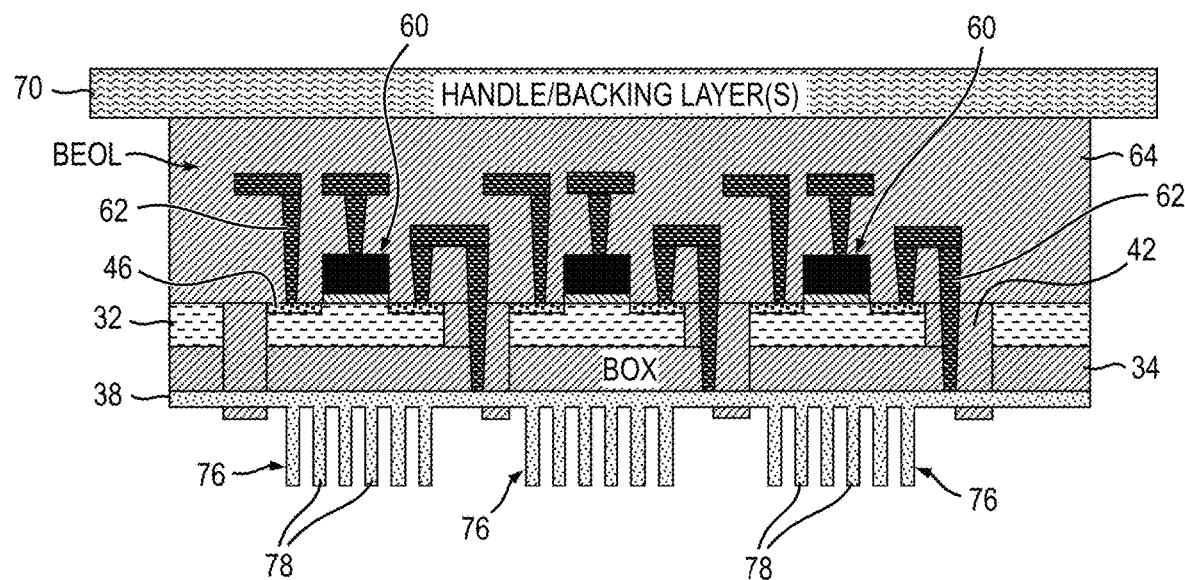
FIG. 7 schematically illustrates patterning and removal of the hard mask to form electrically conductive nanowires or nanofins from the doped layer of the SOI substrate.
Figure 8:
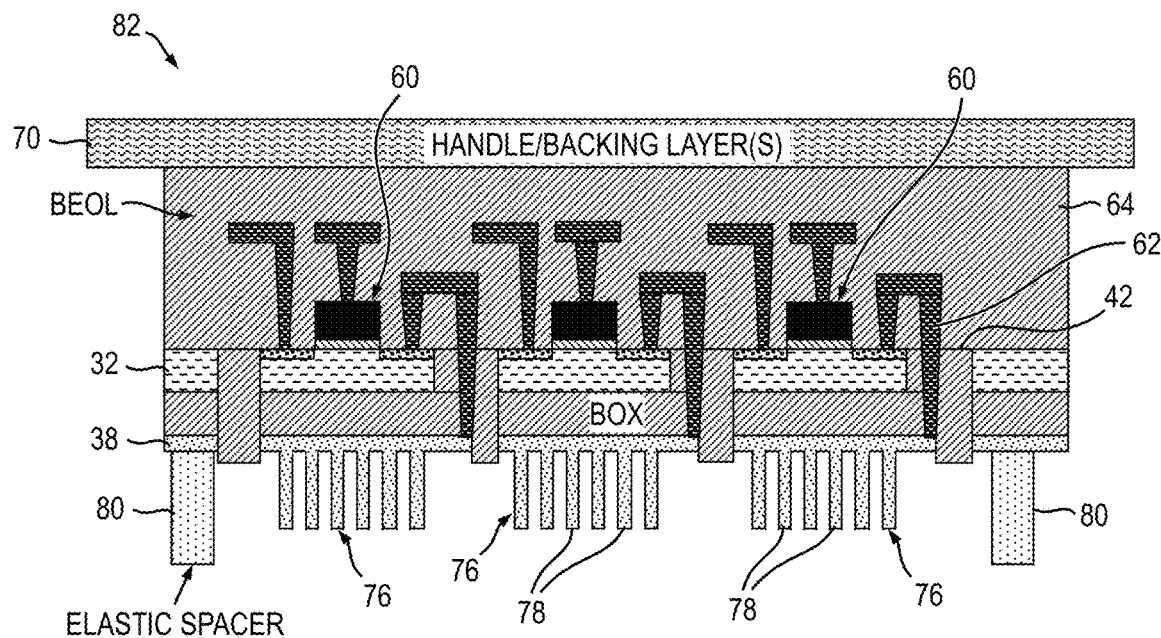
FIG. 8 schematically illustrates the formation of elastic spacers on the SOI substrate.

Spacers 80 are formed on the nanofin/nanowire side of the structure shown in FIG. 7 to obtain a first assembly 82 as shown in FIG. 8. (Alternatively, the spacers may be secured to a second assembly discussed below rather than to the first assembly 82.) The spacers 80 employed in one or more embodiments comprise a resilient material such as a silicone rubber. Polydimethylsiloxane (PDMS) can be employed in some embodiments. Other materials exhibiting elastic properties may alternatively be employed. The lengths of the spacers 80 exceed the lengths of the nanostructures in one or more embodiments. The first assembly 82, as fabricated in accordance with the above discussion, is flexible.

Figure 9:
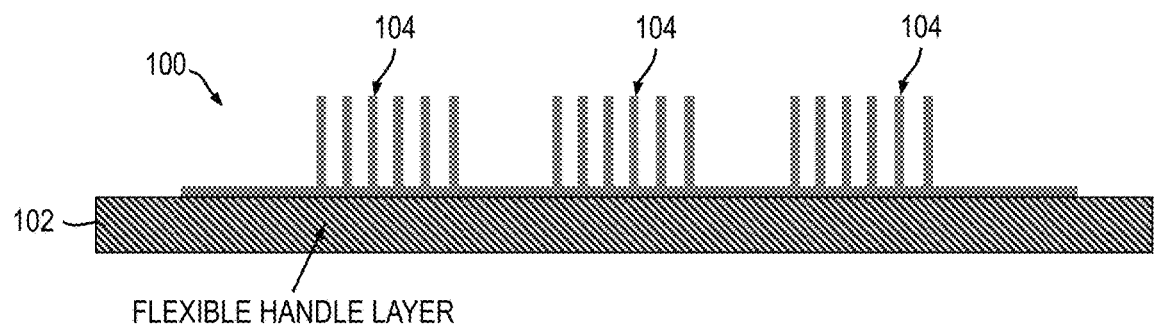
FIG. 9 schematically illustrates formation of arrays of nanofins or nanowires on a second substrate.

FIG. 9 schematically illustrates a second flexible assembly 100 including a flexible handle 102 and arrays 104 of electrically conductive nanowires or nanofins integral with or adhered to the handle. The flexible handle 102 comprises polydimethylsiloxane (PDMS) in one or more embodiments. The handle 102 is not necessarily stretchable. The arrays 104 can be obtained, for example, by forming a molded PDMS structure that includes integral, vertically extending nanowires or nanofins. A silicon nanotemplate can be employed to mold a PDMS handle 102 with such integral arrays of nanowires or nanofins. A thin metal coating (e.g. copper) is then deposited on the side of the structure including the nanowires or nanofins, thereby forming an electrically conductive coating on and between the arrays. As shown in FIG. 9, the illustrated arrays 104 are electrically connected to each other. Alternatively, the nanowire/nanofin arrays can be formed via top-down approaches on a thin, heavily doped silicon film adjoining the handle 102. Techniques similar to those described above with respect to FIGS. 6-7 can be employed to form the arrays 104 of nanostructures such as nanofins or nanowires. The nanostructures of the second assembly 100 have substantially the same dimensions as those of the first assembly 82 in some embodiments.

Figure 10:
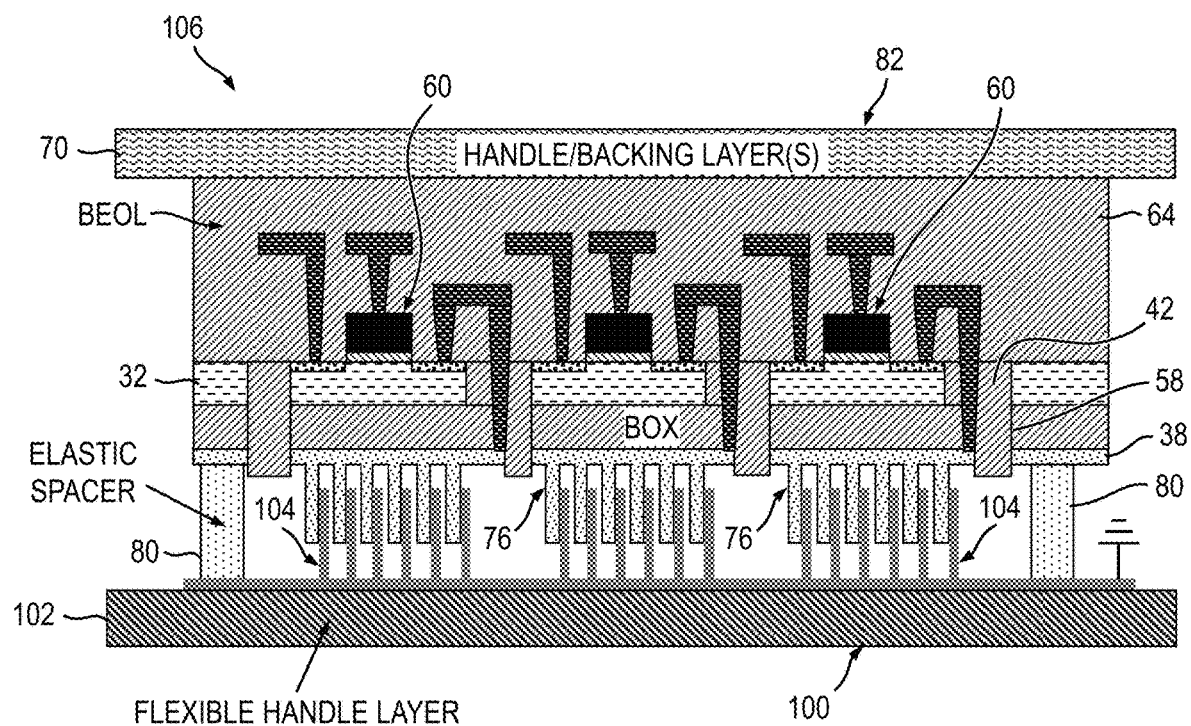
FIG. 10 schematically illustrates assembly of the structures shown in FIGS. 8 and 9 to form an artificial skin assembly.

An exemplary artificial electronic skin assembly 106 is schematically illustrated in FIG. 10. The assembly is comprised of the first and second assemblies 82, 100 mounted such that the nanowire/nanofin sides of each assembly are in opposing relation to each other. The resilient spacers 80 maintain the assemblies at a preselected distance wherein the arrays 76, 104 are interdigitated to form a variable resistor. The arrays 104 on the bottom assembly 100 are connected to a reference potential such as that of a power supply or ground. A voltage point (node) within another system can be employed as a reference potential in some embodiments. The nanostructures of the second flexible assembly 100 are electrically connected to each other and therefore have the same potential. If the active matrix structure is part of another system, that potential can vary over time, but at any given time all of the bottom arrays 104 will still have the same voltage potential. Pressure exerted on the flexible handle 102 causes a change in the spacing between the two assemblies 82, 100 and the extent of contact between the interdigitated nanofins/nanowires of the arrays 76, 104. A change in resistance caused by such pressure allows the detection of changes in the amplitude of the pressure applied using the disclosed active matrix circuitry. Pressure on the bottom assembly will change the total resistance connected to the transistors 60. If the spacers 80 are resilient, pressure exerted on the flexible handle 102 may cause one or more of the spacers to be compressed. The spacers assume their original heights upon release of the pressure. Mechanical flexibility of the assembly 106 facilitates its application to devices requiring non-planar surfaces such as prosthetic devices.

Figure 11:
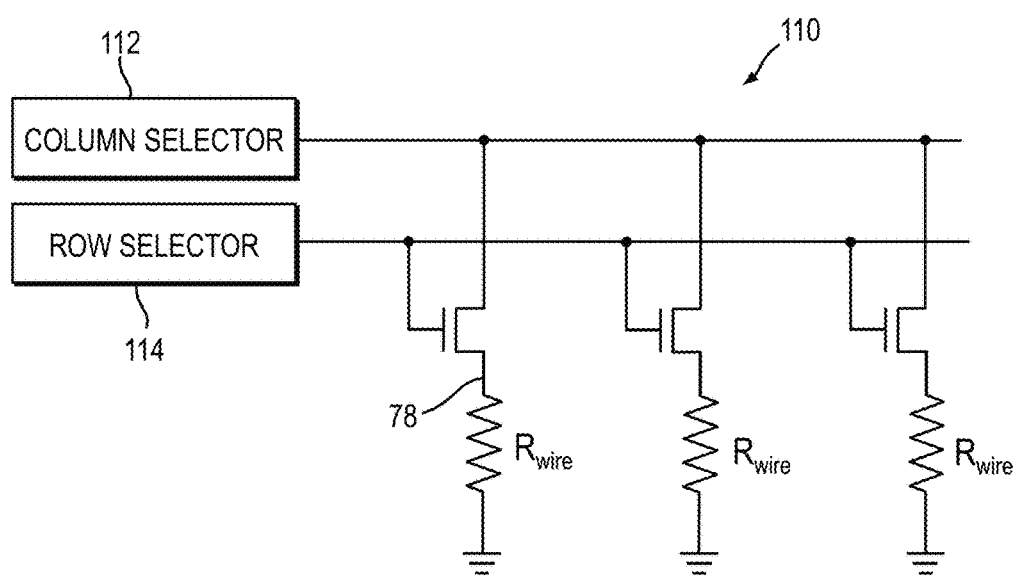
FIG. 11 is a schematic illustration of a circuit using an active matrix structure as shown in FIG. 10.

FIG. 11 schematically illustrates an electrical circuit 110 that can be formed using the elements of the active matrix circuitry described herein. In exemplary embodiments wherein n-type transistors 60 are employed, the interdigitated nanowires or nanofins 78 are electrically connected between the transistor sources and ground. The exemplary circuit further includes a column selector 114 and a row selector 116. The column selector is connected to the transistor drain and the row selector is connected to the transistor gate. Each pixel has a reference circuit (not shown) to correct for drift.

Given the discussion thus far, an exemplary method of fabricating artificial electronic skin includes obtaining a first assembly 82 including a plurality of transistors 60, a semiconductor layer 32, a plurality of active regions within the semiconductor layer, the active regions forming parts of the transistors, and a plurality of electrically isolated first arrays 76 of electrically conductive first nanostructures, each first array being electrically connected to one of the transistors 60. A second assembly 100 including a flexible handle 102 and a plurality of electrically conductive second nanostructures secured to and extending from the flexible handle is further obtained. One or more spacers 80 are positioned between the first and second assemblies. The first assembly 82 is mounted to the second assembly 100, causing the first and second nanostructures of the first and second assemblies to be interdigitated. FIG. 10 shows an exemplary structure obtained using such fabrication steps. In some embodiments, the first assembly 82 is obtained by obtaining a semiconductor-on-insulator substrate 30, the substrate including a semiconductor layer 32, a handle 36, an electrically insulating layer 34 between the semiconductor layer and the handle substrate, and a doped, electrically conductive layer 38 between the handle and the electrically insulating layer. A plurality of electrically isolated active regions is formed within the semiconductor layer. An array of transistors is formed in the active regions using the semiconductor layer 32 of the substrate. Electrical conductors 62 electrically connecting the transistors to the doped, electrically conductive layer 38 are formed and the handle is removed, thereby exposing one or more portions of the doped, electrically conductive layer. A plurality of electrically isolated arrays 76 of vertically extending, electrically conductive nanowires or nanofins 78 ("nanostructures") are formed from the doped, electrically conductive layer 38, each of the arrays 76 of nanowires or nanofins 78 being electrically connected to a transistor 60 in the array of transistors. FIGS. 1-8 show exemplary steps in fabricating the first assembly 82. The step of forming the plurality of first arrays of electrically conductive nanostructures includes, in some embodiments, forming a plurality of arrays of dots or fins over the doped, electrically conductive layer, the dots or fins having etch selectivity with respect to the doped, electrically conductive layer, etching the doped, electrically conductive layer to form nanowires or nanofins from the doped, electrically conductive layer beneath the dots or fins, and removing the dots or fins. In some embodiments, the fabrication method includes electrically connecting the transistors to column and row selectors as shown in FIG. 11.

A further method includes obtaining an artificial electronic skin assembly including a first assembly 82 including a plurality of transistors 60, a semiconductor layer, a plurality of active regions within the semiconductor layer, the active regions forming parts of the transistors, and a plurality of electrically isolated, first arrays 76 of electrically conductive first nanostructures, each first array being electrically connected to one of the transistors. The artificial electronic skin assembly further includes a second assembly 100 including a flexible handle 102 and a plurality of electrically conductive second nanostructures secured to and extending from the flexible handle. The second nanostructures are formed as electrically connected arrays of nanostructures. In some embodiments, the second nanostructures are connected to a reference potential including that of a power supply line or the ground. The first assembly is mounted to the second assembly such that the first nanostructures of the first arrays 76 and the second nanostructures are interdigitated and form variable resistors. The method further includes exerting pressure on the flexible handle 102 in the direction of the first assembly 82, thereby causing relative movement of the interdigitated first and second nanostructures and changing the electrical resistance of one or more of the variable resistors, and detecting the pressure exerted on the flexible handle 102 based on the change in electrical resistance. The change in the electrical resistance arises from the change in the contact area between the first and the second nanostructures. The larger the contact area, the smaller the electrical resistance will be.

An artificial electronic skin assembly includes a first assembly 82 including a plurality of transistors 60, a semiconductor layer 32, a plurality of active regions within the semiconductor layer, the active regions forming parts of the transistors, and a plurality of electrically isolated, first arrays 76 of electrically conductive first nanostructures extending vertically with respect to the semiconductor layer, each first array being electrically connected to one of the transistors. The artificial electronic skin assembly further includes a second assembly 100 including a flexible handle 102 and a plurality of electrically conductive second nanostructures secured to and extending vertically from the flexible handle, the plurality of the second nanostructures being connected to a reference potential. The first assembly is mounted to the second assembly such that the first nanostructures of the first arrays 76 and the second nanostructures are interdigitated and form variable resistors. In some embodiments, the first assembly further includes an electrically insulating layer 34 adjoining a bottom surface of the semiconductor layer, a dielectric layer 64 adjoining a top surface of the semiconductor layer, and a doped silicon-based layer 38 adjoining the electrically insulating layer 34, the doped silicon-based layer including the first nanostructures 78 of the first arrays 76. The first nanostructures have heights ranging between 500 nm-5 µm and widths ranging between 100 nm and 5 µm in some embodiments. The first and second nanostructures comprise nanofins or nanowires in some embodiments. A column selector and a row selector are employed in some embodiments, the transistors being electrically connected to the column and row selectors. Each of the transistors 60 may include doped source/drain regions 46, each of the first arrays 76 of electrically conductive first nanostructures being electrically connected to one of the source/drain regions 46. The plurality of second nanostructures are arranged as a plurality of second arrays 104 on the flexible handle in one or more embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Terms such as "above", "below", "top" and "bottom" are generally employed to indicate relative positions as opposed to relative elevations unless otherwise indicated. It should also be noted that, in some alternative implementations, the steps of the exemplary methods may occur out of the order noted in the figures. For example, two steps shown in succession may, in fact, be executed substantially concurrently, or certain steps may sometimes be executed in the reverse order, depending upon the functionality involved.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
    obtaining an artificial electronic skin assembly including:
        a first assembly including a plurality of transistors, a semiconductor layer, a plurality of active regions within the semiconductor layer, the active regions forming parts of the transistors, and a plurality of electrically isolated, first arrays of first electrically conductive nanostructures, each first array being electrically connected to one of the transistors;
        a second assembly including a flexible handle and a plurality of second electrically conductive nanostructures secured to and extending from the flexible handle, the plurality of the second nanostructures being electrically connected to a reference potential, the first assembly being mounted to the second assembly such that the first nanostructures of the first arrays and the second nanostructures are interdigitated and form variable resistors;
    exerting pressure on the flexible handle in the direction of the first assembly, thereby causing relative movement of the interdigitated first and second nanostructures and changing the electrical resistance of one or more of the variable resistors, and
    detecting the pressure exerted on the flexible handle based on the change in electrical resistance.

2. The method of claim 1, further including conforming the artificial electronic skin assembly to a surface of a prosthetic device such that the flexible handle is exposed.

3. The method of claim 1, wherein the plurality of electrically isolated, first arrays of electrically conductive first nanostructures are comprised of highly doped semiconductor material.

4. The method of claim 3, wherein the plurality of electrically isolated, first arrays of electrically conductive first nanostructures extend vertically with respect to the semiconductor layer and the plurality electrically conductive second nanostructures comprise a plurality of arrays that extend vertically with respect to the flexible handle.

* * * * *